United States Patent [19]

Cortelek et al.

[11] Patent Number: 4,767,796

[45] Date of Patent: Aug. 30, 1988

[54] HARD SEGMENT CONTAINING PREPOLYMERS FROM CYCLOALKANE DIOLS

[75] Inventors: Dolunay I. Cortelek, Meriden; James R. Pritchard, Wallingford, both of Conn.

[73] Assignee: The Dow Chemical Company, Midland, Mich.

[21] Appl. No.: 134,140

[22] Filed: Dec. 17, 1987

[51] Int. Cl.$^4$ ............................................. C08G 18/14
[52] U.S. Cl. ...................... 521/155; 528/60; 528/61; 528/64; 528/65; 528/67; 528/85
[58] Field of Search ............ 521/155; 528/60, 61, 528/64, 65, 67, 85; 252/182.2, 182.22

[56] References Cited

U.S. PATENT DOCUMENTS

| | | | |
|---|---|---|---|
| 3,384,653 | 5/1968 | Erner et al. | 260/453 OR |
| 3,394,164 | 7/1968 | McClellan et al. | 260/453 |
| 3,394,165 | 7/1968 | McClellan et al. | 260/453 |
| 3,644,457 | 2/1972 | König et al. | 260/453 |
| 3,883,571 | 5/1975 | Allport et al. | 260/453 |
| 4,043,982 | 8/1977 | O'Sullivan et al. | 260/47 UA |
| 4,115,429 | 9/1978 | Reiff et al. | 260/453 |
| 4,118,411 | 10/1978 | Reiff et al. | 260/453 |
| 4,229,347 | 10/1980 | Holt et al. | 260/239 A |
| 4,647,623 | 3/1987 | Kase et al. | 525/123 |

FOREIGN PATENT DOCUMENTS

| | | |
|---|---|---|
| 2604060 | 8/1976 | Fed. Rep. of Germany . |
| 1369334 | 10/1974 | United Kingdom . |
| 1377676 | 12/1974 | United Kingdom . |
| 1430455 | 3/1976 | United Kingdom . |
| 1545003 | 4/1979 | United Kingdom . |
| 1577767 | 10/1980 | United Kingdom . |

*Primary Examiner*—Maurice J. Welsh
*Attorney, Agent, or Firm*—James S. Rose

[57] ABSTRACT

Disclosed are novel storage stable liquid compositions derived from heating a liquefied methylenebis(phenyl isocyanate) with a minor proportion of a cycloalkane diol.

The molded polyurethanes produced using the above liquid isocyanates are characterized by excellent resistance to elevated temperatures. In fact, their heat resistance is superior to similarly constituted prior art materials.

11 Claims, No Drawings

4,767,796

HARD SEGMENT CONTAINING PREPOLYMERS FROM CYCLOALKANE DIOLS

FIELD OF THE INVENTION

This invention relates to isocyanate compositions and is more particularly concerned with stable liquid polyisocyanate compositions and the molded polyurethane polymers produced therefrom.

DESCRIPTION OF THE PRIOR ART

Generally speaking, the mechanical and thermal properties of molded polyurethane polymers are directly related to the soft and/or hard segment contents of said polyurethanes. The terms "soft and hard segments" refer to the weight percent proportions of the linkages derived from the polyisocyanate component with high molecular weight (at least 500) active hydrogen containing compounds and low molecular weight (below 400) active hydrogen containing extender compounds, respectively. Furthermore, as is well known in the art, the mutual compatibility or lack thereof between these two types of segments provides further control over resulting polymer properties. It is generally preferable that these two types of segments be thermodynamically incompatible on the molecular or microscopic level while being compatible in the macroscopic phase. Under these conditions the beneficial effects of both types of segments can be realized over a wide temperature range. This means the retention of good tensile modulus properties at low temperatures while having high modulus and good resistance to heat at elevated temperatures.

In the course of the development of this art the use of liquefied isocyanate components has become of increasing importance with the advent of high pressure reactant mixing in the reaction injection molding (RIM) technique. In this connection, methylenebis(phenyl isocyanate) [MDI], which is solid at room temperature, has received the most attention because it offers the optimum combination of good reactivity while yielding products having good physical properties.

Typical of non-urethane containing liquefied MDI are the ones made in accordance with U.S. Pat. No. 3,384,653. Such materials are liquids by virtue of a minor portion of the isocyanate groups being converted to carbodiimide groups. They are generally referred to as carbodiimide-containing polyisocyanates but in point of fact the carbodiimide groups which are generated are in equilibrium with uretoneimine groups arising from the adduct formation between the carbodiimide linkages with isocyanate groups from unreacted MDI. A much greater variety of liquefied MDI products have been disclosed which are in stable liquid form because a minor portion of the isocyanate groups have been reacted with active hydrogen containing components, particularly organic polyols. For example, see U.S. Pat. Nos. 3,394,164; 3,394,165; 3,644,457; 3,883,571; 4,115,429; 4,118,411; 4,229,347; and British Patent Nos. 1,369,334; 1,377,676; 1,430,455; 1,545,003; and 1,577,767. Of these referenced patents some include the use of low molecular weight glycol extender type organic polyols, while others use polyols falling into higher molecular weight categories. It will be noted that the use of such liquefied polyisocyanates serves the dual purpose of providing the liquefied MDI while at the same time providing a means for introducing preformed, hard or soft segments into a polyurethane formulation. This is particularly advantageous with regard to hard segment content in liquefied isocyanates of the type described in U.S. Pat. No. 3,394,164 cited supra. A difficulty encountered with some glycols, for example ethylene glycol, is that even in very small proportions, it is difficult to obtain a storage stable liquid polyisocyanate.

It would indeed be technically advantageous if storage stable liquid isocyanate compositions could be provided which not only are liquid but contain hard segments which result in molded polyurethanes having increased resistance to high temperature environments compared with prior art liquefied polyisocyanates.

U.S. Pat. No. 4,043,982 teaches the preparation of sealants, filling or potting agents or adhesives by the peroxide initiated polymerization of at least one polymerizable monomer. The polymerizable monomers are prepared by reacting an organic polyisocyanate with a polymerizable acrylate ester having a reactive hydrogen atom. Included in the polyisocyanates are higher molecular weight polyisocyanate prepolymers as typically disclosed in Example 1 of said patent. Disclosed therein is the isocyanate prepolymer derived from the reaction of one mole of hydrogenated bisphenol A and two moles of 2,4-toluene diisocyanate.

U.S. Pat. No. 4,647,623 in disclosing non-yellowing urethane paints teaches the preparation of polyisocyanates containing isocyanurate rings by reacting at least one alkylene, cycloalkylene, or aralkylene diisocyanate with a cycloalkylene diol in the presence of a trimerization catalyst.

German patent application DT No. 2604060 discloses prepolymers polymerizable to adhesives or sealants based on polybutadienes, acrylic/methacrylic hydroxyalkyl esters and polyisocyanates wherein the latter include prepolymers of less than half a mole of hydrogenated bisphenol A reacted with a molar proportion of an 80/20 mixture of 2,4- and 2,6-toluenediisocyanate.

SUMMARY OF THE INVENTION

The present invention is directed to isocyanate compositions which are storage stable liquids at ambient temperatures equal to or above about 20° C. which comprise the product obtained by heating a liquefied methylenebis(phenyl isocyanate) with from about 0.02 to about 0.5 equivalent of at least one cycloalkane diol per equivalent of said liquefied methylenebis(phenyl isocyanate).

The invention is also directed to molded polyurethane polymers prepared from an organic polyol, an extender, and a storage stable liquid isocyanate composition described above.

The term "storage stable liquid" means that the composition remains substantially liquid for at least one month when stored at the stated temperature.

The term "liquefied methylenebis(phenyl isocyanate)" means the MDI has been liquefied by converting a minor proportion of the isocyanate groups into free carbodiimide groups or the corresponding uretoneimine adducts thereof or wherein the MDI has been liquefied by reacting from about 2 to about 40 percent of the isocyanate groups with an organic polyol having an active hydrogen functionality of about 2 and a molecular weight of from about 62 to about 4000.

The term "methylenebis(phenyl isocyanate)" means 4,4'-methylenebis(phenyl isocyanate) and mixtures thereof with up to about 30 percent of the 2,4'-isomer.

The term "cycloalkane diol" means a diol obtained by replacing two nuclear hydrogen atoms of a cycloalkane by —OH groups said cycloalkane having from 4 to 12 cycloaliphatic carbon atoms and the resulting radical is inclusive of cyclobutylene, cyclopentylene cyclohexylene, cycloheptylene, cyclooctylene radicals, and cycloalkane diols having the formula:

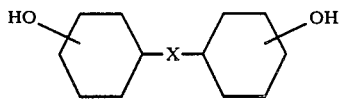

wherein X is selected from the group consisting of a direct bond, —SO$_2$—, —CO—, —O—, and lower-alkylene. The term cycloalkane diol also comprehends unsaturated diols provided the unsaturation is not at the ring carbon atoms bearing hydroxyl substituents.

The term "lower alkylene" means alkylene having 1 to 4 carbon atoms, inclusive, such as methylene, ethylene, propylene, butylene, isopropylidene, isobutylene, and the like.

Surprisingly, the above described storage stable liquid isocyanate compositions do result in molded polyurethanes having enhanced resistance to high temperature environments compared with those products derived from prior art liquefied MDI materials. None of the prior references noted above comprehend the present products.

DETAILED DESCRIPTION OF THE INVENTION

The isocyanate compositions in accordance with the present invention are readily prepared simply by bringing together the starting liquefied methylenebis(phenyl isocyanate) [hereinafter MDI] and the cycloalkane diol in any desired manner. Generally speaking, the cycloalkane diols are solids at room temperature (circa 20° C. to 25° C.) so it is essential that those diols which are solids be completely dissolved in the liquid MDI. Both the dissolution and reaction are advantageously achieved by heating the components at a temperature of from about 30° C. to about 150° C., preferably from about 45° C. to about 100° C. Because of the well known sensitivity of isocyanate to atmospheric moisture, it is preferable that air and moisture be excluded during the reaction process. This is typically achieved by carrying out the heating during some type of mixing or agitation under an inert atmosphere, for example, nitrogen or argon. The time required to complete the urethane forming reaction between the isocyanate and hydroxyl groups will obviously vary depending upon the temperatures employed, the particular reactivity and solubility of the diol, whether a urethane catalyst is employed, and the like. The course of the reaction can be followed by the disappearance of hydroxyl functionality and the heating step can be carried out until all of the cycloaliphatic hydroxyls are consumed as measured by any conventional analytical procedure such as infrared analysis, nuclear magnetic resonance, vapor phase chromatography, and the like.

If desired, an inert solvent may be employed. The term "inert solvent" means any organic solvent that does not react with the isocyanate or hydroxyl groups or otherwise interfere with the urethane forming reaction. Typical but non-limiting of such solvents are aromatic hydrocarbons such as benzene, toluene, xylene, chlorobenzene, nitrobenzene, and the like; dipolar aprotic solvents such as dimethyl sulfoxide, dimethyl formamide, dimethyl acetamide, hexamethyl phosphoramide, tetramethyl urea, and the like. Generally speaking, however, their use is neither necessary nor recommended because of the additional cost and inconvenience involved.

As noted above, the reaction period will be influenced by, inter alia, the presence or absence of a urethane catalyst. Accordingly, and, optionally, any urethane catalyst known to those skilled in the art may be used in catalytic amounts, for example, from about 0.001 percent by weight to about 5.0 percent by weight based on total weight of liquefied MDI and cycloalkane diol. Such catalysts include organic and inorganic acid salts of, and organometallic derivatives of, bismuth, lead, tin, iron, antimony, uranium, cadmium, cobalt, thorium, aluminum, mercury, zinc, nickel, cerium, molybdenum, vanadium, copper, manganese and zirconium, as well as phosphines and tertiary organic amines. Representative organotin catalysts are stannous octoate, stannous oleate, dibutyltin diacetate, dibutyltin dioctoate, dibutyltin dilaurate, dibutyltin maleate, dibutyltin mercaptopropionate, dibutyltin didodecylmercaptide, dibutyltin bis(isoctylthioglycolate), and the like. Representative tertiary organic amine catalysts are triethylamine, triethylenediamine, N,N,N',N'-tetramethylethylenediamine, N,N,N',N'-tetraethylethylenediamine, N-methylmorpholine, N-ethylmorpholine, N,N,N',N'-tetramethylguanidine, N,N,N',N'-tetramethyl-1,3-butanediamine, N,N-dimethylethanolamine, N,N-diethylethanolamine, N,N-dimethylcyclohexylamine, and the like, and mixtures of the above in any combination.

The novel and distinguishing feature of the present compositions over those in the art cited supra, and, the reason for their polyurethane products having higher heat resistance, lies in the cycloalkane diol employed. The cycloalkane diol component may be a single diol or mixture of more than one diols. It is to be understood that the cyclic ring may contain unsaturation and/or may be substituted by inert groups in addition to the two hydroxyls. The term "inert group" means any group that does not react with hydroxyl and isocyanate groups or otherwise interfere with the polyurethane reaction. Typical of such inert groups are C$_1$ to C$_8$ alkyl, nitro, C$_1$ to C$_8$ alkoxy, halo inclusive of fluorine, chlorine, bromine, and iodine, cyano and the like.

A preferred group of such diols includes the cyclohexylene diols, the isopropylidenebis(cyclohexanols), and mixtures of these classes. Most preferred are the isopropylidenebis(cyclohexanols).

Illustrative but non-limiting of the diols are 1,3-cyclobutanediol, 1,3-cyclopentanediol, 1,3-cyclohexanediol, 1,4-cyclohexanediol, 2-cyclohexene-1,4-diol, 2-methyl-1,4-cyclohexanediol, 2-ethyl-1,4-cyclohexanediol, 1,3-cycloheptanediol, 1,4-cycloheptanediol, 2-methyl-1,4-cycloheptanediol, 4-methyl-1,3-cycloheptanediol, 1,3-cyclooctanediol, 1,4-cyclooctanediol, 1,5-cyclooctanediol, 5-methyl-1,4-cyclooctanediol, 5-ethyl-1,4-cyclooctanediol, 5-propyl-1,4-cyclooctanediol, 5-butyl-1,4-cyclooctanediol, 5-hexyl-1,4-cyclooctanediol, 5-heptyl-1,4-cyclooctanediol, 5-octyl-1,4-cyclooctanediol, and the like; 4,4'-methylenebis(cyclohexanol), 4,4'-methylenebis(2-methylcyclohexanol), 4,4'-methylenebis(3-methylcyclohexanol), 3,3'-methylenebis(cyclohexanol), 4,4'-ethylenebis(cyclohexanol), 4,4'-propylenebis(cyclohexanol), 4,4'- butylenebis(cyclohexanol), 4,4'-isopropylidenebis(cyclohexanol), 4,4'-isobutylenebis(cyclohexanol), 4,4'-dihydroxydicyclohexyl, 4,4'-carbonylbis(cyclohexanol), 3,3'-carbonylbis(cyclohexanol), 4,4'-sulfonylbis(cyclohexanol), 4,4'-oxybis(cyclohexanol), and the like; and mixtures of any of the above. Preferred of the above species are those falling within the definition of cyclohexylene diols and 4,4'-isopropylidenebis(cyclohexanols), particularly the latter.

The proportions within which the diol component is employed, as noted above falls within a range of from about 0.02 to about 0.5 equivalent per equivalent of MDI. Preferably, the range is from about 0.05 to about 0.3, most preferably from about 0.05 to about 0.25 equivalent.

The liquefied MDI component defined above can be any of the liquid products known in the art and as typically disclosed in U.S. Pat. Nos. 3,384,653; 3,394,164; 3,394,165; 3,644,457; 3,883,571; 4,115,429; 4,118,411; and 4,229,347, cited supra. The liquid MDI products disclosed in these U.S. patents are hereby incorporated herein by reference. Also, the liquid MDI products disclosed in the British Patents cited supra can be used in the present compositions. It is to be understood that the MDI products can be based on the pure 4,4'-isomer and mixtures of the 4,4'-isomer with up to 30 percent of the 2,4'-isomer. The majority of the liquid MDI materials are derived from the reaction of minor proportions of hydroxyl, for example, from about 0.02 to about 0.4 equivalent with an equivalent of the solid MDI. The hydroxyl containing molecules range from low molecular weight glycols (MW=62-400) to high molecular weight glycols (MW 500 to 4000). Mixtures of these along with additional and very minor amounts of trifunctional polyols can be employed.

However, the most preferred liquid MDI components are those well known liquid products commonly referred to as carbodiimide-containing MDI materials. These are typically exemplified in U.S. Pat. No. 3,384,653 whose disclosure is already incorporated herein. Liquefaction of the starting MDI is brought about by treating the diisocyanate with a carbodiimide forming catalyst until a minor proportion of the isocyanate groups are converted to the carbodiimide linkage (—N=C=N—). Under room temperature environments, for example less than 25° C., the carbodiimide linkage cyclizes with an isocyanate from another MDI molecule to form the uretoneimine adduct which can break down at elevated temperatures to the carbodiimide and isocyanate components. A preferred liquefied MDI according to this process for use in the present compositions has sufficient of the isocyanate groups converted to carbodiimide so that the isocyanate equivalent falls within a range of from about 130 to about 180, preferably from about 130 to about 150.

As noted above, the present isocyanate compositions are storage stable liquids at ambient temperatures of 20° C. and higher. The compositions are mobile liquids characterized by a viscosity falling within a range of from about 2000 to bout 15,000 cps at 25° C., preferably from about 4000 to about 10,000 cps.

In addition to being mobile liquids, the compositions retain their fluidity for at least one month upon storage at ambient temperatures (circa 20° C.). Generally speaking, they retain this fluidity for much longer periods. Furthermore, if exposed to lower temperatures, i.e. 10° C. to 15° C., they will become viscous but are easily liquefied upon warming back up to ambient conditions.

These fluid characteristics make the present compositions particularly useful in the preparation of molded polyurethanes by the RIM procedure.

As an additional, and, unexpected benefit to flow from the present compositions, the molded polyurethanes prepared with them as the isocyanate component have dramatically higher heat resistance then prior art polyurethanes lacking the hard segments based on the cycloalkane diols. This higher heat resistance is determined by heat sag determinations as defined in footnote 9 of Table I below and heat deflection temperatures measured in accordance with ASTM Test D-648.

The preparation of the molded polyurethanes in accordance with the present invention can be carried out using any of the conventional methods for the preparation of polyurethanes except for the replacement of the organic polyisocyanate by the isocyanate compositions described hereinabove. A particularly preferred mode of preparation is by the RIM procedure. For illustrative and detailed teaching in respect of RIM methods including reactants and molding procedures reference is made to U.S. Pat. Nos. 4,218,543; 4,296,212; 4,374,210; 4,433,067; and 4,659,747 whose disclosures relative thereto are incorporated herein by reference.

High molecular weight compounds having at least two active hydrogen containing groups such as polymeric polyols or polymeric amines having molecular weights of from about 1500 to about 12,000 and active hydrogen functionality of from about 2 to about 6 are reacted with the isocyanate component, preferably, in combination with low molecular weight extenders having molecular weights of from about 62 to about 400 including glycols and diamines. Generally speaking, the high molecular weight active hydrogen compounds (polyols, and the like) are present such that their equivalent proportions to the total equivalents of low molecular weight extenders fall within the range of about 1:4 to about 1:100, preferably from about 1:10 to about 1:60. Furthermore, the equivalent proportions of the liquid polyisocyanate compositions of the invention to the total active hydrogen equivalents comprised of the high molecular weight polyols, polyamines, and the extender are such that the ratio of isocyanate equivalents to total active hydrogen equivalents falls within a range of from about 0.85:1 to about 1.20:1, preferably from about 0.95:1 to about 1.10:1.

Any of the polyols and polyamines disclosed in the patents cited supra whose disclosures are incorporated herein and which meet the definition set forth above can be employed as the high molecular weight component. It will be obvious to one skilled in the art that when polyols are employed the resulting molded polymers contain high percentages of polyurethane linkages, whereas polyurea linkages arise from the polyamines. In the event that the polyamines are the ingredients chosen then the polymer would contain high percentages of polyurea linkages.

In respect of the polymeric polyol component, the functionality is, preferably, from about 2 to about 4 with the hydroxyl functionality predominantly primary and a molecular weight from about 1500 to about 7000. Most preferably, the polyols have a functionality of about 2 to about 3 and M.W. from about 2000 to about 6000.

A preferred group of polyols comprises the polypropyleneoxy-polyethyleneoxy capped diols and triols obtained by the alkoxylation of water, ammonia, ethylene glycol, propylene glycol, trimethylolpropane, glycerine, aniline, ethanolamine, and the like; polyester diols obtained from the reaction of dibasic carboxylic acids such as succinic, adipic, suberic, azelaic, phthalic, isophthalic, and the like with alkylene glycols, and oxyalkylene glycols to form the corresponding polyalkylene, and polyoxyalkylene ester diols or copolymers thereof; and the vinyl-resin reinforced propyleneoxyethyleneoxy capped diols and triols, particularly those polyethers reinforced with polyacrylonitrile.

In respect of the polymeric polyamine component, the functionality is, preferably, from about 2 to about 4, wherein greater than 50 percent of the active hydrogens are primary and/or secondary amines. Most preferably, the polyamines are the predominantly primary amine terminated polyethyleneoxy-polypropyleneoxy polyethers having a functionality of about 2 to about 3 and molecular weight from about 2000 to about 6000. This class of compounds is typically disclosed in U.S. Pat. No. 4,433,067 already incorporated herein.

It will be evident to those skilled in the art that the present polymers and methods comprehend the use of prepolymer technology wherein the isocyanate reactive components, particularly the organic polyols, can be prereacted in minor amounts with excess isocyanate composition prior to the final polymer forming RIM step.

Typical of such extenders defined above but non-limiting are ethylene glycol, 1,4-butanediol, 1,6-hexanediol, 1,4-cyclohexanedimethanol, neopentyl glycol, bis(2-hydroxyethyl)ethers of hydroquinone and resorcinol, hexamethylene diamine, octamethylene diamine, 2,4-diaminotoluene, 2,6-diaminotoluene, 4,4'-diamino-3,3'-dichlorodiphenylmethane, 2,4-diamino-3,5-diethyl toluene, 2,6-diamino-3,5-diethyl toluene, and mixtures of two or more of any of the above.

In its broadest aspect, the present invention includes molded polyurethanes wherein the major proportion of the linkages are urethanes per se. In a preferred embodiment of the present polymers, either a high molecular weight polyamine as defined above, or, and most preferably, a diamine extender either alone or in combination with a glycol is employed with a polyol to provide a polyurethane-polyurea polymer.

Preferably a urethane catalyst is employed. Typical of the catalysts are those already set forth above. The preferred catalysts are the organometallic compounds particularly the dialkyltin salts such as the dibutyltin compounds noted above. The catalyst proportions can fall within the percentage ranges set forth above but based on the total polymer formulation.

Optionally, blowing agents may be employed even in the production of molded polyurethanes wherein compact tough skinned surfaces are desired. Any of the blowing agents known to those skilled in the art can be used including water and fluorocarbon blowing agents. The latter are preferred and generally are halogenated aliphatic hydrocarbons which can be also substituted by chlorine and/or bromine in addition to the fluorine content.

Also, inert gases (e.g. nitrogen) may be introduced at the polymer forming stage to provide whatever degree of blowing is desired from microcellular to macrocellular in nature.

Other optional additives such as dispersing agents, internal mold release agents, cell stabilizers, surfactants, flame retardants, colorants, fillers such as fiber glass and the like can be added to the polyurethane polymers in accordance with the present invention.

The polymers produced in accordance with the present invention are characterized by the excellent properties of impact strength, tensile, hardness, heat resistance, and modulus properties. However, it is in their heat resistance wherein the unexpected advantage lies. By virtue of the introduction of the hard segments arising from the cycloalkane diols their heat deflection temperatures and heat sags are dramatically better when compared with prior art materials.

Accordingly, the molded polyurethane articles in accordance with the present invention find particular utility as auto parts such as car bumpers, body elements, panels, doors, engine hoods, skirts, air scoops, and the like which require exposure to high temperatures during painting operations. Further, the thermosetting nature of the present polymers results in their good high temperature performance characteristics which make them suitable for industrial elastomer applications where high temperature resistance is needed.

The following examples describe the manner and process of making and using the invention and set forth the best mode contemplated by the inventors of carrying out the invention but are not to be construed as limiting.

EXAMPLE 1

An isocyanate composition in accordance with the present invention is prepared as follows. A 2 gallon size reactor is charged with 2100 g. of a liquefied sample (I.E.=about 144) of 4,4'-methylenebis(phenyl isocyanate) prepared by heating the starting MDI with a carbodiimide forming catalyst until the above stated I.E. is reached. The liquid MDI is heated to about 62° C. and during continuous stirring under a blanket of nitrogen 240 g. of solid 4,4'-isopropylidenebis(cyclohexanol) is added at the rate of about 10 g. per 15 minutes over a 6 hour period. The reaction mixture is maintained at the 62° C. mark until all of the solid bis(cyclohexanol) material is dissolved. Heating is continued for an additional 2 hour period at 62° C. Upon cooling to ambient temperature (about 20° C.) a clear mobile liquid isocyanate composition is obtained having an I.E.=187.2; viscosity determined as averages of three separate determinations at three separate temperatures: at 20° C.=7243 cps; at 25° C.=4087 cps; at 38° C.=1203 cps.

In a separate but related experiment which is carried out similarly to the above reaction, 6364 g. of the same carbodiimide-containing liquid MDI is reacted with 636 g. of the 4,4'-isopropylidenebis(cyclohexanol) in a 12 liter reactor at a temperature of 65° C. In this experiment the finely powdered bis(cyclohexane) is added over a 2 day period. The liquefied MDI reactant is maintained between 65° and 75° C. The product is a clear mobile liquid: I.E.=about 186; viscosity=7510 cps (19° C.).

Another isocyanate composition in accordance with the present invention is prepared by heating together 12 g. of 4,4'-isopropylidenebis(cyclohexanol) and 252 g. of the liquefied MDI described above at 60° C. for 2 hours. Upon cooling to room temperature the product remained a mobile liquid; I.E.=161.3.

In yet another isocyanate composition of this invention, 306 g. of the above described liquefied MDI is heated with 60 g. of the 4,4'-isopropylidenebis(cyclohexanol) at 90° C. for 4 hours. The mobile liquid product has a viscosity of 7500 cps. (25° C.) and I.E.=242.

EXAMPLE 2

The following experiment describes the reaction injection molding (RIM) preparation of three high flexural modulus polyurethane-polyurea containing elastomers in accordance with this invention (runs 1 to 3), along with three comparison RIM polyurethane-polyureas (runs 1C to 3C). A pilot plant scale RIM machine is employed with the ingredients in the proportions in parts by weight set forth in Table I.

One tank of the RIM machine is charged with the A component (at 38° C.) while a second tank is charged with the B component (at 43° C.). Metering pumps from each tank are used to deliver the ingredients into the impingement mixing head of the RIM machine. After mixing, the reaction mixture is directed into an aluminum mold measuring 10 inches×18 inches×⅛th inch. Mold temperature is 107° C. with the shot time being 1.51 seconds. Demold time is 30 seconds and all samples are postcured for 0.5 hour at 163° C.

Identical B components are used in all moldings including the series of runs 1 to 3 and the comparison series 1C to 3C. Isocyanate blends are used in both series wherein two particular polyisocyanates are common to both blends. A third component in the Isocyanate II of series 1C to 3C is a liquefied methylenebis(phenyl isocyanate) of the prior art whereas the third component in the Isocyanate I of series 1 to 3 is a liquid isocyanate composition in accordance with the present invention and prepared as set forth in Example 1 above. The descriptions of the various isocyanate components are set forth in the footnotes to Table I below.

The properties of each run of the invention can be compared with its respective comparison runs 1C to 3C. The noteworthy feature is the fact that the direct replacement of the hard segments of the 1C to 3C samples by the hard segments of the (a) component in the Isocyanate I of runs 1 to 3 gives rise to a dramatic increase in high temperature properties of the latter polymers over the comparison materials. This is shown by the overall superior Heat Sags particularly at 325° F. of the runs 1 to 3 as opposed to 1C to 3C.

TABLE I

| Run | 1 | 1C | 2 | 2C | 3 | 3C |
|---|---|---|---|---|---|---|
| Ingredients (pts. by wt.) | | | | | | |
| Component A: | | | | | | |
| Isocyanate I[1] | 543 | — | 573.2 | — | 601 | — |
| Isocyanate II[2] | — | 540 | — | 569.9 | — | 598 |
| Component B: | | | | | | |
| Polyol[3] | 123 | 123 | 123 | 123 | 123 | 123 |
| 1,4-Cyclohexanedimethanol | 125 | 125 | 125 | 125 | 125 | 125 |
| DETDA[4] | 125 | 125 | 125 | 125 | 125 | 125 |
| UL-28[5] | 0.05 | 0.05 | 0.05 | 0.05 | 0.05 | 0.05 |
| L-550[6] | 3.7 | 3.7 | 3.7 | 3.7 | 3.7 | 3.7 |
| Oleoyl sarcosine | 5.5 | 5.5 | 5.5 | 5.5 | 5.5 | 5.5 |
| Zinc stearate | 13.76 | 13.76 | 13.76 | 13.76 | 13.76 | 13.76 |
| T-403[7] | 13.76 | 13.76 | 13.76 | 13.76 | 13.76 | 13.76 |
| NCO/OH Index | 0.95 | 0.95 | 1 | 1 | 1.05 | 1.05 |
| Properties: | | | | | | |
| Density (gm/cc) | 1.169 | 1.169 | 1.172 | 1.171 | 1.172 | 1.176 |
| Hardness, Shore D | 80 | 80 | 81 | 79 | 81 | 77 |
| Notched Izod[8] (ft-lbs/in.) | 3.19 | 4.83 | 3.24 | 3.73 | 2.31 | 4.44 |
| Flex. modulus, kpsi | 248 | 258 | 246 | 254 | 273 | 280 |
| Flex. strength, psi | 12,840 | 12,699 | 11,940 | 13,010 | 13,614 | 13,118 |
| Heat sag[9] | | | | | | |
| 275° F./1 hr. | 0.12 | 0.08 | 0.07 | 0.16 | 0.07 | 0.13 |
| 325° F./1 hr. | 0.1 | 0.44 | 0.21 | 0.33 | 0.19 | 0.48 |
| Tensile strength, psi | 6801 | 6918 | 7072 | 6968 | 7500 | 7745 |
| % Elongation | 16.5 | 21 | 17.4 | 16.6 | 16.7 | 36 |
| HDT (°C.)[10] at 264 psi | 150 | — | 143 | — | 158 | — |

Footnotes to Table I
[1] Isocyanate I: A polyisocyanate blend of overall I.E. = 173 to 174 comprising: (a) 40 percent by weight of a polyisocyanate prepolymer of the present invention (I.E. = about 185) prepared by the procedure set forth in Example 1 above; (b) 40 percent by weight of a polyisocyanate prepolymer (I.E. = about 173) prepared by the reaction of a mixture of (i) about 81.6 percent by weight of the liquefied form of 4,4'-methylenebis(phenyl isocyanate) in which a portion of the isocyanate groups have been converted to carbodiimide groups to the extent that the I.E. = about 144 and (ii) 18.4 percent of an ethyleneoxy capped (about 18% E.O.) polypropyleneoxy triol of eq. wt. = 1650; and (c) 20 percent by weight of the liquefied diisocyanate described under (bi) above.
[2] Isocyanate II: A polyisocyanate blend identical to Isocyanate I above including same I.E. except the component (a) is replaced by a 40 percent by weight proportion of a liquefied methylenebis(phenyl isocyanate)(I.E. = about 181) prepared from 4,4'-methylenebis(phenyl isocyanate) and a mixture of equal parts by weight of dipropylene glycol and tripropylene glycol wherein the total hydroxyl equivalent is about 0.2 per equivalent of isocyanate.
[3] Polyol: A 2000 eq. wt. polyethyleneoxy capped (about 13%) polypropyleneoxy triol.
[4] DETDA: A mixture of 80/20 percent by weight of 1-methyl-3,5-diethyl-2,4-diaminobenzene and 1-methyl-3,5-diethyl-2,6-diaminobenzene, respectively.
[5] UL-28: A dimethyltin dialcoholate urethane catalyst: supplied by Witco Chemical Corporation.
[6] L-550: Silicone surfactant for nucleation assistance; supplied by Union Carbide Corporation.
[7] T-403: Amine terminated polyether triamine; amine E.W. = 150; supplied by Texaco Corporation; serves as compatibilizer for zinc stearate.
[8] Notched Izod impact strength measured in accordance with ASTM D256-56.
[9] Heat Sag: Determined by measuring the amount in inches that a one inch wide sample (about ⅛ inch thick) with a six inch unsupported overhang droops under its own weight when held at one end in a horizontal position at the temperatures and time set forth above.
[10] HDT is the heat deflection temperature measured in accordance with ASTM Test Method D-648.

EXAMPLE 3

This experiment describes the RIM preparation of three high flexural modulus polyurethane-polyurea containing elastomers in accordance with the present invention (runs 4 to 6) along with three comparison RIM polyurethane-polyureas (runs 4C to 6C). A different but similarly designed pilot plant RIM machine is employed with the ingredients in the proportions in parts by weight set forth in Table II.

The procedure and conditions are the same as described in Example 2 using the same component temperatures, and shot times of 1.5 seconds to fill a steel mold measuring 12 inches by 12 inches by ⅛ inch. Demold time is 30 seconds with the individual mold temperatures set forth in Table II.

The molded runs 4, 5, 4C and 5C can be considered as one comparable set of polymers as all these samples have a 50/50 w/w mixture of diol/diamine extenders. Runs 6 and 6C can be considered as another comparable set with the diol/diamine mixture being 60/40. Run 4 has as its sole isocyanate component Isocyanate III in accordance with the invention. Runs 5 and 6 employ Isocyanate I described in footnote 1 of Table I. Contrastingly, 4C and 6C have a mixture of Isocyanates IV and V while 5C employs Isocyanate VI. These latter three isocyanates are not of the invention and are identified in the footnotes in Table II.

The HDT and Heat Sag values for runs 4, 5, and 6 are all superior to their comparison materials 4C, 5C and 6C. These superior values are particularly striking for run 1 wherein the polyol proportion is higher than any of the other samples.

TABLE II

| Run | 4 | 5 | 4C | 5C | 6 | 6C |
|---|---|---|---|---|---|---|
| Ingredients (pts. by wt.) | | | | | | |
| Component A: | | | | | | |
| Isocyanate III[1] | 477.7 | — | — | — | — | — |
| Isocyanate I[2] | — | 564.2 | — | — | 575.8 | — |
| Isocyanate IV[3] | — | — | 235.3 | — | — | 236.8 |
| Isocyanate V[4] | — | — | 353.0 | — | — | 355.2 |
| Isocyanate VI[5] | — | — | — | 463.8 | — | — |
| Component B: | | | | | | |
| Polyol[6] | 150 | 123 | 100 | 163 | 123 | 100 |
| 1,4-Cyclohexanedi-methanol | 100 | 125 | 125 | 125 | 150 | 150 |
| DETDA | 100 | 125 | 125 | 125 | 100 | 100 |
| UL-28 | 0.05 | 0.05 | 0.10 | 0.05 | 0.05 | 0.05 |
| Mold Temp °C. | 152 | 140 | 135 | 152 | 118 | 93 |
| NCO/OH Index | 1.00 | 1.00 | 1.00 | 1.00 | 1.00 | 1.00 |
| Properties: | | | | | | |
| Density (gm/cc) | 1.167 | 1.165 | 1.174 | 1.152 | 1.153 | 1.180 |
| Hardness, Shore D | — | 79 | 80 | 77 | 78 | 77 |
| Notched Izod (ft-lbs/in.) | 3.80 | 4.43 | 4.50 | 4.46 | 4.02 | 4.53 |
| Flex. modulus, kpsi | 239.5 | 265.1 | 249.0 | 242.3 | 266.8 | 233.0 |
| Flex. strength, psi | 14.2 | 14.4 | 13.1 | 12.9 | 13.5 | 13.7 |
| Heat sag | | | | | | |
| 275° F./1 hr. | 0.02 | −0.03 | 0.07 | 0.05 | 0.23 | 0.22 |
| 325° F./1 hr. | 0.07 | 0.10 | 0.15 | — | 0.26 | 1.15 |
| Tensile strength, psi | 7879 | 8120 | 8110 | 6710 | 7289 | 7570 |
| % Elongation | 16 | 15 | 34 | 26 | 17 | 52 |
| HDT (°C.) at 264 psi | 163 | 151 | 137 | 140 | 134 | 118 |

Footnotes to Table II
[1]Isocyanate III: The polyisocyanate prepolymer of the present invention (I.E. = about 185) identified as component (a) of Isocyanate I described in footnote 1 of Table I and prepared by the procedure set forth in Example 1 above.
[2]Isocyanate I: Described in footnote 1 of Table I above.
[3]Isocyanate IV: is the liquefied 4,4'-methylenebis-(phenyl isocyanate) described as component (a) of Isocyanate II described in footnote 2 of Table I.
[4]Isocyanate V: is the polyisocyanate prepolymer described as component (b) of Isocyanate I, footnote 1 of Table I.
[5]Isocyanate VI: is the liquefied carbodiimide-containing 4,4'-methylenebis(phenyl isocyanate)described as the (bi) component of Isocyanate I, footnote 1 of Table I.
[6]Polyol: is the polyether triol described in footnote 3 of Table I.

We claim:

1. An isocyanate composition which is a storage stable liquid at ambient temperatures equal to or above about 20° C. which composition comprises the product obtained by heating a liquefied methylenebis(phenyl isocyanate) with from about 0.02 to about 0.5 equivalent of at least one cycloalkane diol per equivalent of said liquefied methylenebis(phenyl isocyanate).

2. A composition according to claim 1 wherein said heating is carried out in a range of from about 30° C. to about 150° C.

3. A composition according to claim 1 wherein said liquefied methylenebis(phenyl isocyanate) comprises a carbodiimide containing methylenebis(phenyl isocyanate).

4. A composition according to claim 1 wherein said cycloalkane diol is selected from the group consisting of cyclohexylene diols, isopropylidenebis(cyclohexanols), and mixtures thereof.

5. A composition according to claim 1 wherein said cycloalkane diol is an isopropylidenebis(cyclohexanol).

6. An isocyanate composition which is a storage stable liquid at ambient temperatures equal to or above about 20° C. which composition comprises the product obtained by heating at a temperature of from about 30° C. to about 150° C. a mixture comprising
    (a) a liquefied carbodiimide-containing methylenebis-(phenyl isocyanate); and
    (b) from about 0.02 to about 0.5 equivalent of an isopropylidene(cyclohexanol) per equivalent of said methylenebis(phenyl isocyanate).

7. A composition according to claim 6 wherein said liquefied methylenebis(phenyl isocyanate) has an isocyanate equivalent weight of from about 130 to about 180 and is derived from 4,4'-methylenebis(phenyl isocyanate).

8. A composition according to claim 7 wherein said diol is 4,4'-isopropylidenebis(cyclohexanol).

9. A composition according to claim 8 wherein the proportions of said diol are from about 0.05 to about 0.3 equivalent per equivalent of said liquefied 4,4'-methylenebis(phenyl isocyanate).

10. A molded polyurethane polymer prepared from an organic polyol, an extender, and a liquid isocyanate composition according to claim 1.

11. A reaction injection molded polyurethane-polyurea prepared from an organic polyol, a diamine extender, and a liquid isocyanate composition according to claim 1.

* * * * *